(12) United States Patent
Braginsky et al.

(10) Patent No.: US 6,409,016 B1
(45) Date of Patent: Jun. 25, 2002

(54) HOLDER AND DISPENSER FOR SPOOLS, TUBE-SHAPED DEVICES, AND CYLINDRICAL DEVICES WITH RECESSED ENDS

(75) Inventors: Michael Braginsky, Newton; Joan Goldberg, Somerset; John J. Piekos, Assonet, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/604,383

(22) Filed: Jun. 27, 2000

(51) Int. Cl.[7] .............................................. B65D 85/00
(52) U.S. Cl. ....................... 206/397; 206/63.3; 206/482
(58) Field of Search ................................ 206/63.3, 227, 206/380, 389, 397, 408, 476–478, 480–483; 229/87.01, 155

(56) References Cited

U.S. PATENT DOCUMENTS

| | | | | |
|---|---|---|---|---|
| 1,930,311 A | * | 10/1933 | Gittleman ................... 206/482 |
| 2,043,070 A | * | 6/1936 | Rutkowski ................... 206/482 |
| 3,136,418 A | | 6/1964 | Stacy et al. |
| 3,487,922 A | * | 1/1970 | Peck ........................... 206/478 |
| 4,555,016 A | * | 11/1985 | Aday et al. ................. 206/63.3 |
| 5,020,660 A | * | 6/1991 | Akerley et al. ............. 206/397 |
| 5,359,831 A | | 11/1994 | Brown et al. ................. 53/430 |
| 5,439,102 A | | 8/1995 | Brown et al. ............... 206/63.3 |
| 5,529,175 A | * | 6/1996 | Brunken ..................... 206/63.3 |
| 5,788,062 A | | 8/1998 | Cerwin et al. ............. 206/63.3 |
| 5,896,982 A | | 4/1999 | Surcin et al. |
| 5,988,367 A | | 11/1999 | Gemma, Jr. et al. ....... 206/63.3 |
| 6,016,905 A | | 1/2000 | Gemma et al. ............ 206/63.3 |
| 6,196,389 B1 | * | 3/2001 | Buetter et al. .............. 206/397 |

* cited by examiner

*Primary Examiner*—Jim Foster
(74) *Attorney, Agent, or Firm*—Richard D. Allison; Thomas J. DesRosier

(57) ABSTRACT

Featured is a device for holding spools, tube-shaped devices with various cross-section configurations, and cylindrical devices with recessed ends such as surgical suture spools and a means of manufacturing the device, wherein the device provides greater stability to the spool, tube-shaped device or cylindrical device with recessed ends and the means of manufacture does not require any major modifications to the current packaging process for the spool, tube-shaped device and cylindrical device alone. Moreover, when the device is a holder and dispenser for armed surgical sutures, the surgical suture needle is visible and readily accessible.

40 Claims, 3 Drawing Sheets

HOLDER AND DISPENSER FOR SPOOLS, TUBE-SHAPED DEVICES, AND CYLINDRICAL DEVICES WITH RECESSED ENDS

FIELD OF INVENTION

The present invention relates to a holder and dispenser for spools, tube-shaped devices, and cylindrical devices with recessed ends that firmly and securely holds and stabilizes the spool, tube-shaped device with various cross-section configurations, or cylindrical devices with recessed ends attached thereto and a process of manufacturing the holder and dispenser; but more particularly, this invention is directed to holders and dispensers for spools, tube-shaped surgical devices, and cylindrical devices with recessed ends, especially holders and dispensers for surgical sutures with a needle attached thereto, which needles are visible and readily accessible.

BACKGROUND OF THE INVENTION

The prior art includes numerous methods of packaging sutures for use in a surgical procedure. A few examples of suture packaging devices includes Brown et al. (U.S. Pat. No. 5,359,831), which discloses a molded suture container for retaining and dispensing absorbable and non-absorbable surgical sutures; Brown et al. (U.S. Pat. No. 5,566,821), which discloses a folded paper or plastic surgical suture retaining package device that delivers surgical sutures, which are wound in an hourglass configuration, in a controlled and tangle-free manner; Cerwin et al. (U.S. Pat. No. 5,788,062), which discloses a suture coil in an inexpensive paper or plastic dispenser with a rigid winding fixture; and Gemma et al. (U.S. Pat. No. 6,016,905), which discloses sutures wound in a figure eight configuration in a plastic snap-lock suture container. Recent innovations in suture dispensers include cylindrical spools, containing fixed length, pre-knotted surgical sutures, which allow faster, easier and more secure endoscopic suturing. As an example, these dispensers may be used in various laparoscopic procedures such as a cholecystectomy or splenectomy, in which having a pre-tied knot is desirable.

Presently, armed suture spools, which is to say spools of sutures with a surgical suture needle attached thereto, come packaged in a sterilized blister, pouch or bag. When sutures are needed in a surgical procedure, an armed suture spool is placed into a sterile area from which it can be grabbed and used as needed. However, the spool itself is unstable and can roll freely. Moreover, grabbing the needle may be awkward as the needle must first be located and then picked up from the surgical area. Therefore, a need exists for a cylindrical spool holder that is stable, that facilitates grabbing a suture needle, and that quickly and easily dispenses sutures.

SUMMARY OF THE INVENTION

The present invention features an innovative device for holding and dispensing spools, tube-shaped devices with various cross-section configurations, and cylindrical devices with recessed ends, and, more particularly, spools containing armed surgical sutures and, furthermore, a method of manufacturing the device. The holder and dispenser disclosed in the instant invention confines a spool, tube-shaped device, or cylindrical device with recessed ends between a pair of tabs, stabilizing the spool, tube-shaped device, or cylindrical device with recessed ends and, further, preventing it from rolling freely. Furthermore, the holder and dispenser disclosed herein retains a surgical suture needle in a location where it can be readily seen and easily grabbed. The instant invention, moreover, allows the spools, tube-shaped devices and cylindrical devices with recessed ends to be sterilized and packaged without requiring major modifications in the packaging materials or processes that are presently used in packaging the spools, tube-shaped devices and cylindrical devices with recessed ends alone.

Therefore, it is an object of the present invention to provide a device for holding spools, tube-shaped devices, and cylindrical devices with recessed ends that stabilize the spool, tube-shaped device or cylindrical device with recessed ends contained thereon, preventing it from rolling.

It is another object of the present invention to provide a device for holding armed surgical sutures spools, tube-shaped devices or cylindrical devices with recessed ends that holds a surgical suture needle so it is visible and can be accessed easily.

It is a further object of the present invention to provide a simple means of manufacturing the holding and dispensing device for spools, tube-shaped devices or cylindrical devices.

It is yet another object of the present invention to provide a means of packaging the new device without requiring major modifications in the packaging materials or processes that are presently used for packaging the spools, tube-shaped devices and cylindrical devices with recessed ends alone.

The present invention attains the foregoing and additional objects by retaining a spool, tube-shaped device or cylindrical device with recessed ends in a folded blank device, which secures the spool, tube-shaped device or cylindrical device with recessed ends between a pair of tabs, minimizing translation in a lateral or longitudinal direction; and, furthermore, which safely secures the tip of a surgical suture needle where it is visible and can be accessed easily. Moreover, the present invention allows one to package the new device without requiring major changes to the packaging process that was performed on the spools, tube-shaped devices or cylindrical devices by themselves.

Other aspects and embodiments of the invention are discussed below. Moreover, additional objects and advantages of the present invention are apparent from the drawings and specifications that follow.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
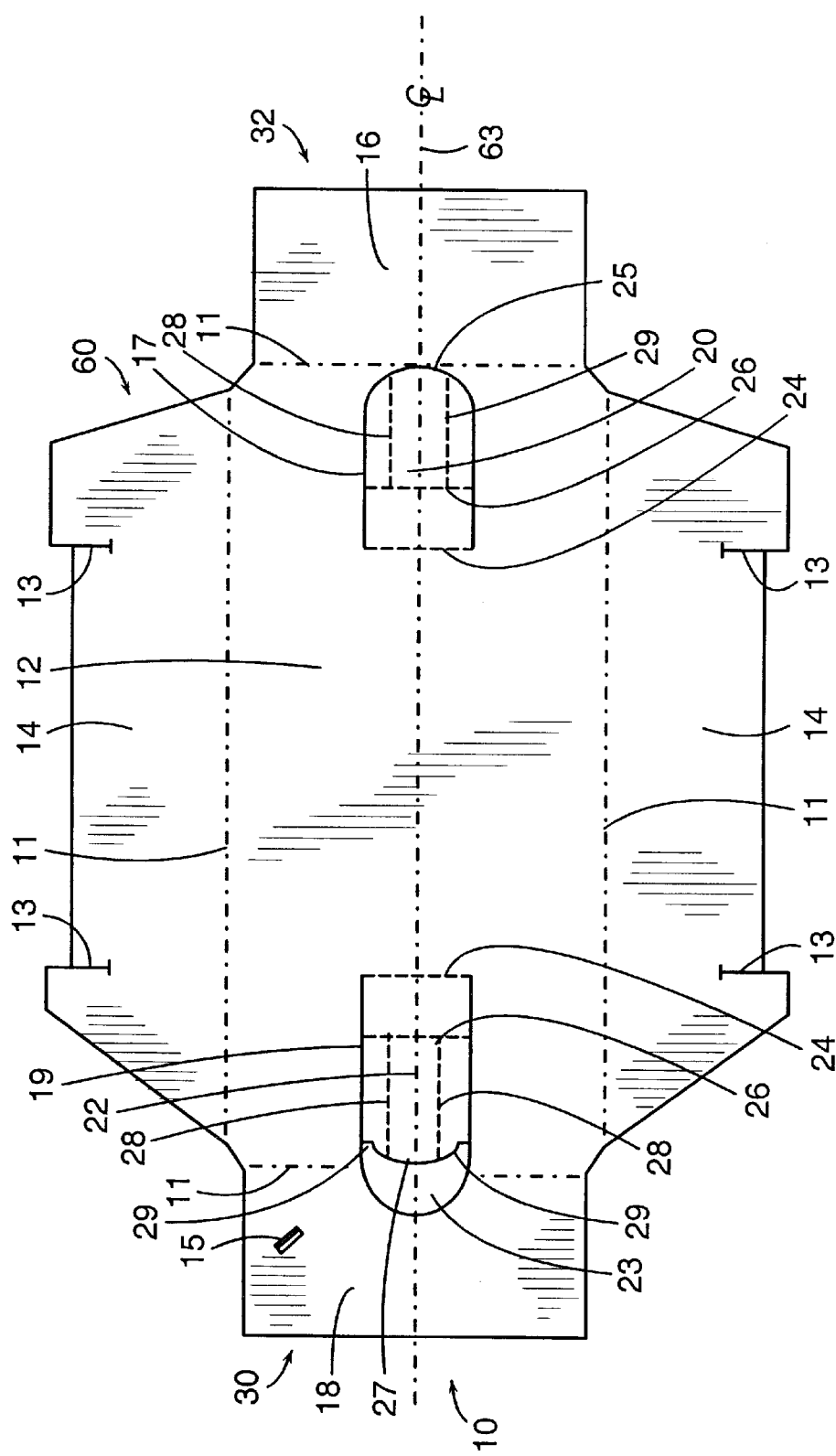
FIG. 1 is a plain view of an embodiment of the holding device blank.
Figure 2:
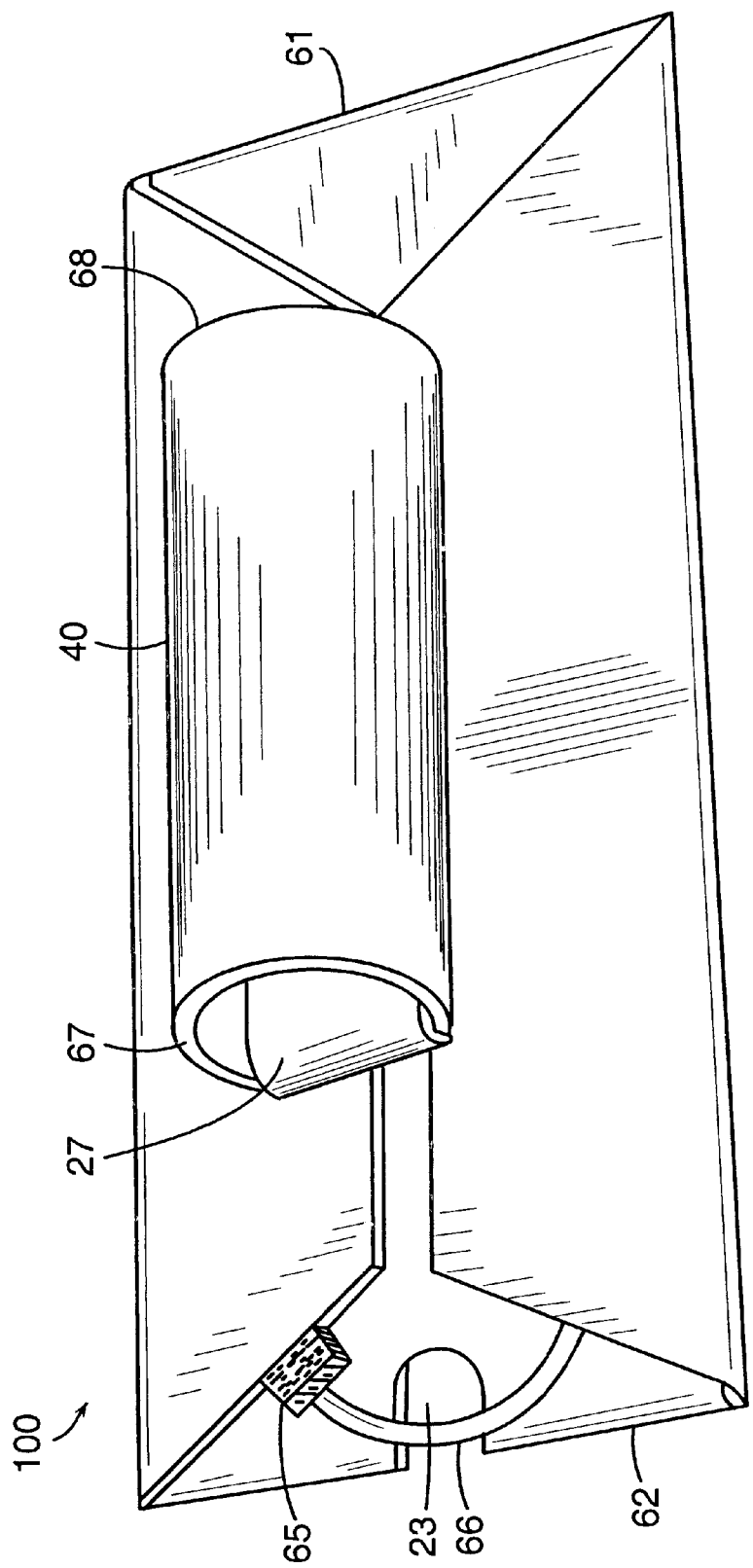
FIG. 2 is a perspective view of an embodiment of the assembled device retaining a tube-shaped surgical device.

Referring now to the various figures of the drawing wherein like reference characters refer to like parts, there is shown in FIG. 1 a plan view of the holding device blank 10, which has a certain shape around a perimeter 60. The device blank 10 typically is die cut and made of paper, rigid plastic film, corrugated board, cardboard or any other pliable material that can be folded to form a compact holder without adhesives, tapes or staples. In the preferred embodiment, the device blank 10 is fabricated from 9-point paper. The perimeter 60 and dimensions thereof may vary to hold spools, tube-shaped devices or cylindrical devices with recessed ends of virtually any length or diameter.

The device blank 10 comprises a plurality of primary scoring or perforation lines 11 that segregate the device blank 10 into a base panel 12, a pair of symmetrical side flaps 14, a solid end flap 16, and a windowed end flap 18, which are manipulated in a manner describe in greater detail below to create a holding and dispensing device 100 for a spool, tube-shaped device or cylindrical device with recessed ends 40. A pair of slits 13 is made on the pair of symmetrical side flaps 14 as a securing means, which also is described in greater detail below. A small slit for a needle 15 is made through the windowed end flap 18, or, in the alternate, a small foam pad 65 is adhesively attached to the reverse side of the windowed end flap 18 for holding a surgical suture needle 66 safely and securely.

The base panel 12 has a plurality of slits 17, 19 and , which create, respectively, a tab 20 and a windowed tab 22 at a proximal 6 land a distal end 62 of the base panel 12. The slit 17, which produces the tab 20, is symmetrical about the centerline 63 of the base panel 12. The slit 17 can be configured to produce a tab 20 of any shape or dimension. In the preferred embodiment, the tab 20 has a rounded, circular end 25. The slit 19, which produces an opening 23 generally between the windowed end flap 18 and the windowed tab 22, is symmetrical about the centerline 63 of the base panel 12. The opening 23 can be any shape or dimension. In the preferred embodiment, the opening 23 is crescent-shaped. The windowed tab 22 also can be any shape or dimension. In the preferred embodiment the windowed tab 22 has a rounded, circular end 27 with a pair of wings 29, intended to ease the material stripping for making a hole.

Secondary scoring or perforation lines 24, 26 on the tab 20 and on the windowed tab 22 facilitate folding the tab 20 and the windowed tab 22 for insertion into apertures at a distal 67 and proximal end 68 of a spool, tube-shaped device or cylindrical device with recessed ends 40. Tertiary scoring or perforation lines 28, 29 on the tab 20 and on the windowed tab 22 provide flexibility to use the same holder on spools, tube-shaped devices or cylindrical devices with recessed ends that have smaller diameters or end openings. When squeezed between the thumb and index finger, the tertiary scoring or perforation lines 28, 29 bend sufficiently to facilitate inserting the tab 20 and the windowed tab 22 into apertures with a smaller diameter or end opening at a distal 67 and proximal end 68 of a spool, tube-shaped device or cylindrical device with recessed ends 40.

Manufacture of the holding and dispensing device 100 is simple, requiring minimal automation. The device blank 10 is placed on any flat surface. The tab 20 and the windowed tab 22 are folded upwards, rotating generally about scoring line 24. The tip of tab 25 and the tip of windowed tab 27 are then folded, generally downward and towards each other, rotating about scoring or perforation line 26. The tip of the tab 25 and the tip of the windowed tab 27 are then inserted into apertures at the distal 67 and proximal end 68 of a spool, tube-shaped device or cylindrical device with recessed ends 40.

If the spool, tube-shaped device or cylindrical device with recessed ends 40 contains surgical sutures with a surgical needle 66 attached thereto, the device blank 10, with a spool, tube-shaped device or cylindrical device with recessed ends 40 attached loosely thereto, is placed on a fixture equipped with a pair of posts. The posts are guided through a pair of holes in the bottom panel 12, which are created when the tab 20 and windowed tab 22 are folded up and inserted in the spool, tube. shaped device or cylindrical device with recessed ends 40. The free-running end of the sutures is then wound loosely around the posts until the suture needle 66 is near the windowed end flap 18. The device blank 10 is then removed carefully from the fixture and the sutures rest loosely on the bottom panel 12.

The windowed end flap 18 is then folded about scoring or perforation line 11 approximately 180 degrees, or until the edge of the windowed end flap 30 contacts or nearly contacts the base of the windowed tab 22 at the secondary scoring or perforation line 24, covering the end loops of the suture windings. In like manner, the solid end flap 16 is folded about scoring or perforation line 11 approximately 180 degrees, or until the edge of the solid end flap 32 contacts or nearly contacts the base of the tab 20 at the secondary scoring or perforation line 24, covering the end loops of the suture windings. The tab 20 and the windowed tab 22, which are bowed slightly due to the weight of the spool, tube-shaped device or cylindrical device with recessed ends 40, respectively, prevent the solid end flap 16 and the windowed end flap 18 from unfolding upwards. Moreover, the solid end flap 16 and the windowed end flap 18, respectively, lock the tab 20 and the windowed tab 22 in position, restricting movement longitudinally in the direction of the centerline 63. A suture needle 66 is then inserted into the small slit 15, so that the suture needle 66 traverses the crescent-shaped opening 23 in the windowed end flap 18. In another embodiment, the suture needle 66 is inserted into a foam pad 65, adhesively affixed to the windowed end flap 18. This positioning of the suture needle 66 allows one to see the suture needle 66 clearly and to grab the suture needle 66, eg., with forceps easily.

The pair of symmetrical side flaps 14 is then folded about scoring or perforation line 11 approximately 180 degrees, until the base of the tab 20 and the base of the windowed tab 22 are inserted in the pair of slits 13 on each of the symmetrical side flaps 14, covering the suture windings. The base of the tab 20 and the base of the windowed tab 22 that are in communion with the slits 13 frictionally prevent the pair of side flaps 14 from unfolding upwards. The pair of side flaps 14 restricts lateral movement about the centerline 63 of the base portion 12, and, in combination with the end flaps 16, 18, further restricting longitudinal movement in the direction of the centerline 63 of the base portion 12, providing greater stability to the holding and dispensing device 100. The holding and dispensing device 100 can then be sterilized and inserted in a bag, pouch, or blister, hereinafter collectively referred to as packaging.

Packaging of the holding and dispensing device is an important part of the invention especially when the spool, tube-shaped device or cylindrical device with recessed ends is a tube-shaped surgical device containing armed surgical sutures. Indeed, the claimed invention precludes redesigning packaging materials that are currently used to package armed suture spools by themselves. Packaging protects the holding and dispensing device from chemical, mechanical, or microbiological degradation in shipping, storage or handling. Indeed, the qualities most desirable in packaging for such use are ease of opening and protection from degradation and/or contamination.

Absorbable sutures, which can be degraded by a process called hydrolysis, must be hermetically sealed in moisture impervious material, e.g., metal or aluminum foil pouch, which is heat sealed. Typically, the metal or aluminum foil pouch is further placed and sealed in a pouch made of medical grade paper and polyester/polypropylene sheeting to provide a second layer of protection. Non-absorbable sutures, which are not subject to degradation from hydrolysis, typically do not require hermetic sealing in moisture impervious material. Instead, it is perfectly acceptable to store non-absorbable sutures in a mylar/tyvek pouch, which is heatsealed.

Figure 3:
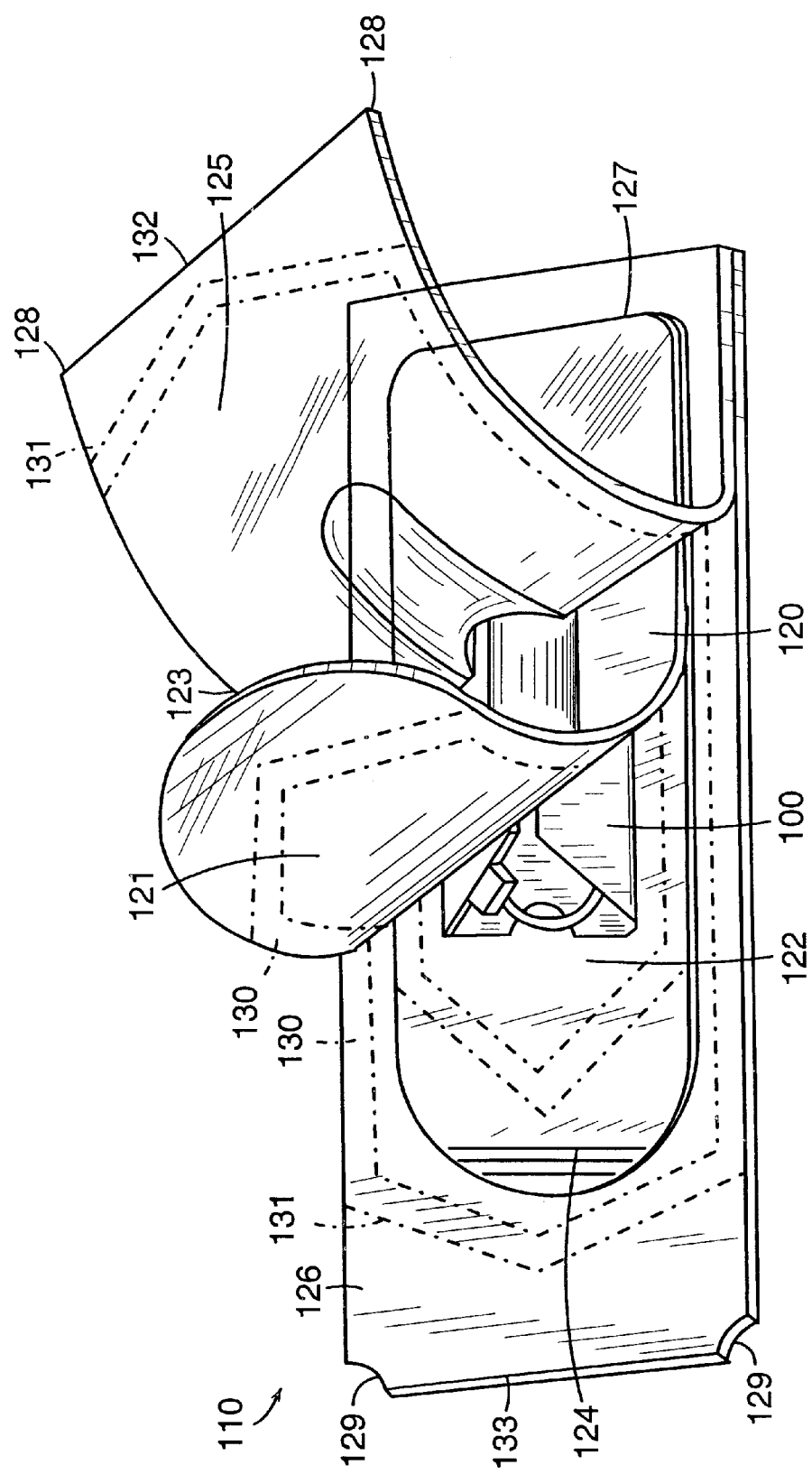
FIG. 3 is a perspective view of an embodiment of a packaging container

The preferred embodiment of packaging for a holding and dispensing device 100 for absorbable sutures is shown in FIG. 3. Absorbable sutures are protected by a dual packaging system 110. The innermost package comprises a peelable moisture impervious barrier 120, which has an upper side 121 and a lower side 122. The moisture impervious barrier 120 typically is made of metal, e.g., aluminum, foil. The upper side 121 and the lower side 122 of moisture impervious barrier 120 are hermetically sealed 130, eg., by heat or adhesive, to protect absorbable sutures from hydrolysis. Non-absorbable sutures do not require a moisture impervious barrier 120.

The end of the upper side 123 and the end of the lower side 124 of the peelable moisture barrier 120 are not sealed. Instead, the end of the upper side 123 and the end of the lower side 124 of the peelable moisture barrier 120 have a tactile feel, es, ripples, to facilitate grabbing and separating the two ends 123, 124. Indeed, the two ends 123, 124 can be grabbed with the thumb and index finder of each hand and opened easily with a small force produced when the thumb and index finger of each hand move in opposite directions to one another, breaking the hermetic seal 130 progressively.

A peelable outermost package 127 typically is made of a combination of medical grade paper and polyester/propylene sheeting. The upper side 125 and the lower side 126, of the peelable outermost package 127 are hermetically sealed, e.g., by heat or adhesive, to provide an additional layer of protection to the contents therein. The end of the upper side 132 and the end of the lower side 133 of the peelable outermost package 127 are not sealed. Furthermore, the edges of the end of the upper side 132 and the end of the lower side 133 are serrated to facilitate separating the two ends 132, 133 with one's thumbs. To further facilitate separating the end of the upper side 132 and the end of the lower side 133 from each other, at least one corner 129 of the end of the lower side 126 is removed to expose at least one corner of the end of the upper side 128. The end of the upper side 132 and the end of the lower side 133 of the outermost package 127 can be grabbed with the thumb and index finder of each hand and opened easily with a small force produced when the thumb and index finger of each hand move in opposite directions to one another. The preferred embodiment of packaging for non-absorbable, which do not require a moisture impervious barrier, comprises a peelable outermost package 127 described above.

When the holding and dispensing device 100 contains armed, absorbable, surgical sutures, one embodiment of the method of using this invention comprises, first, removing the packaging 110 to expose the holding and dispensing device 100 by peeling back, first, the ends of the upper side 132 and lower side 133 of the outermost package 125, and, subsequently, peeling back the ends of the upper side 123 and the lower side 124 of the moisture impervious barrier 121. Once the holding and dispensing device 100 has been exposed, it can be placed or dropped on a sterile field. When armed surgical sutures contained on the holding and dispensing device 100 are needed during a medical operation, a pair of forceps, or similar medical instrument, secures the surgical needle 66. The spool 40 is forcibly removed from the restraining tab 20 and windowed tab 22 by manually pulling the spool 40 away from the holding and dispensing device 100. The suture windings, which are contained beneath the end flaps 16, 18 and pair of side flaps 14, are then forcibly extended and removed from the holding and dispensing device 100.

Although a preferred embodiment of the invention has been described using specific terms, such description is for illustrative purposes only, and it is to be understood that changes and variations may be made without departing from the spirit or scope of the following claims.

What is claimed is:

1. A medical device including a spool, tube-shaped device or cylindrical device with recessed ends and a device blank with a distal and proximal end that is approximately symmetric about a centerline, wherein the device blank further comprises:

a. a plurality of primary folding lines, wherein the primary folding lines segregate the device blank into a base panel and a plurality of flaps; and b. at least two slits, that are made in the base panel, wherein the slits define a tab and a windowed tab, which can be inserted into a distal and proximal end of the spool, tube-shaped device or cylindrical device.

2. A medical device as in claim 1, wherein the plurality of primary folding lines are scoring lines.

3. A medical device as in claim 1, wherein the plurality of primary folding lines are perforation lines.

4. A medical device as in claim 1, wherein the device blank is fabricated from a material that can be folded.

5. A medical device as in claim 4, wherein the material is cardboard.

6. A medical device as in claim 4, wherein the material is corrugated board.

7. A medical device as in claim 4, wherein the material is rigid plastic film.

8. A medical device as in claim 4, wherein the material is paper with a thickness.

9. A medical device as in claim 8, wherein the thickness of the paper is nine-point.

10. A medical device as in claim 1, wherein the plurality of flaps further comprises a pair of side flaps, a windowed end flap, and a solid end flap.

11. A medical device as in claim 10, wherein a pair of slits is incised into the pair of side flaps near a distal and proximal end thereof.

12. A medical device as in claim 10, wherein a small opening with a shape is cut symmetrically into the windowed end flap about the centerline.

13. A medical device as in claim 10, wherein a small slit to retain the tip of a surgical suture needle is incised into the windowed end flap.

14. A device for holding spools, tube-shaped devices or cylindrical devices with recessed ends, comprising a device blank with a distal and proximal end that is approximately symmetric about a centerline, wherein the device blank further comprises:

a plurality of primary folding lines, wherein the primary folding lines segregate the device blank into a base panel and a plurality of flaps; and at least two slits, that are made in the base panel, wherein the slits define a tab and a windowed tab, which can be inserted into a distal and proximal end of a spool, tube-shaped device or cylindrical device with recessed ends wherein the plurality of flaps further comprises a pair of side flaps, a windowed end flap, and a solid end flap; and wherein a small foam pad to retain the tip of a surgical suture needle is adhesively affixed to the windowed end flap.

15. A device for holding spools, tube-shaped devices or cylindrical devices with recessed ends, comprising a device blank with a distal and proximal end that is approximately symmetric about a centerline, wherein the device blank further comprises:

a plurality of primary folding lines, wherein the primary folding lines segregate the device blank into a base panel and a plurality of flaps; and at least two slits, that are made in the base panel, wherein the slits define a tab and a windowed tab, which can be inserted into a distal and proximal end of a spool, tube-shaped device or cylindrical device with recessed ends; and wherein at least one of said tabs, comprises a hinged end, a free end that has shape, an upper and a lower secondary folding line, and a pair of tertiary folding lines.

16. A device for holding spools, tube-shaped devices or cylindrical devices with recessed ends as in claim 15, wherein the shape of the free end is semicircular.

17. A device for holding spools, tube-shaped devices or cylindrical devices with recessed ends as in claim 15, wherein the folding lines are scoring lines.

18. A device for holding spools, tube-shaped devices or cylindrical devices with recessed ends as in claim 15, wherein the folding lines are perforation lines.

19. A device for holding spools, tube-shaped devices or cylindrical devices with recessed ends as in claim 15, wherein the secondary folding lines are approximately perpendicular to the centerline.

20. A device for holding spools, tube-shaped devices or cylindrical devices with recessed ends as in claim 15, wherein the lower secondary folding line intersects the base panel at the hinged end.

21. A device for holding spools, tube-shaped devices or cylindrical devices with recessed ends as in claim 15, wherein the tertiary folding lines are approximately parallel to the centerline.

22. A device for holding spools, tube-shaped devices or cylindrical devices with recessed ends as in claim 15, wherein the tertiary folding lines extend continuously from the free end to the upper secondary folding line.

23. A method of manufacturing a device for holding a surgical device, having a pair of apertures;

wherein the device comprises a device blank formed with a distal and a proximal end that is approximately symmetric about a centerline, wherein the method of manufacturing the device blank further comprises:

a. forming a plurality of primary folding lines, wherein the primary folding lines segregate the device blank into
i. a base panel,
ii. a pair of side flaps,
wherein a pair of slits are incised on each pair of side flaps;
iii. a windowed end flap is formed, having an edge, at the proximal end of the device blank, which has a retaining means thereon;
wherein a small opening is cut with a shape that is approximately symmetrical about the centerline; and iv. a solid end flap is formed, having an edge, at the distal end of the device blank; and b. at least two slits are formed that penetrate the base panel,
wherein the slits define a tab at the distal end of the device blank;
wherein the tab comprises a hinged end, a free end, an upper and a lower secondary folding line, and a pair of tertiary folding lines;
and a windowed tab at the proximal end of the device blank;
wherein the windowed tab comprises a hinged end, a free end, an upper and a lower secondary folding line, and a pair of tertiary folding lines.

24. A method of manufacturing a device for holding a surgical device as in claim 23, wherein the surgical device is formed as a spool.

25. A method of manufacturing a device for holding a surgical device as in claim 23, wherein the folding lines are formed as scoring lines.

26. A method of manufacturing a device for holding a surgical device as in claim 23, wherein the folding lines are formed as perforation lines.

27. A method of manufacturing a device for holding a surgical device as in claim 23, wherein the surgical device is formed as a tube-shaped device with various cross-section configurations.

28. A method of manufacturing a device for holding a surgical device as in claim 23, wherein the surgical device is formed as a cylindrical device with recessed ends.

29. A method of manufacturing a device for holding a surgical device as in claim 23, wherein the surgical device is formed as a spool of armed surgical sutures.

30. A method of manufacturing a device for holding a surgical device, having a pair of apertures;

wherein the device comprises a device blank with a distal and a proximal end that is approximately symmetric about a centerline, wherein the device blank further comprises:

a plurality of primary folding lines, wherein the primary folding lines segregate the device blank into
iii. a base panel,
iv. a pair of side flaps,
wherein a pair of slits is incised on each pair of side flaps;
iii. a windowed end flap, having an edge, at the proximal end of the device blank, which has a retaining means thereon;
wherein is cut a small opening with a shape that is approximately symmetrical about the centerline; and
iv. a solid end flap, having an edge, at the distal end of the device blank; and at least two slits that penetrate the base panel,
wherein the slits define a tab at the distal end of the device blank;
wherein the tab comprises a hinged end, a free end, an upper and a lower secondary folding line, and a pair of tertiary folding lines;
and a windowed tab at the proximal end of the device blank;
wherein the windowed tab comprises a hinged end, a free end, an upper and a lower secondary folding line, and a pair of tertiary folding lines;
wherein the steps of manufacture comprise:
a. folding the tab upward by rotating the free end of the tab about the lower secondary folding line at the hinged end of the tab;

b. folding the windowed tab upward by rotating the free end of the windowed tab about the lower secondary folding line at the hinged end of the windowed tab;

c. folding the tab inward about the upper secondary folding line, forming a tab tip;

d. folding the windowed tab inward about the upper secondary folding line, forming a windowed tab tip;

e. inserting the tab tip and windowed tab tip into the pair of apertures of the surgical device;

f. folding the windowed end flap upward and inward approximately 180 degrees until the edge of the windowed end flap is near the lower secondary folding line of the windowed tab;

g. folding the solid end flap upward and inward approximately 180 degrees until the edge of the solid end flap is near the lower secondary folding line of the tab; and h. folding the pair of side flaps upward and inward approximately 180 degrees until the tab and the windowed tab are inserted in the pair of slits.

31. A method of manufacturing a device for holding a surgical device as in claim 30, further comprising the following steps, which occur between steps e and f, when the surgical device is a spool of armed surgical sutures, which has a free running end with a surgical suture needle attached thereto:

a. placing the device blank on a fixture comprising a pair of posts, wherein the pair of posts are inserted into a pair of openings that are created when the tab and windowed tab are folded upward; and b. wrapping loosely about the pair of posts the free running end of the armed surgical sutures.

32. A method of manufacturing a device for holding a surgical device as in claim 30, further comprising the following steps, which occur between steps g and h, when the surgical device is a spool of armed surgical sutures, which has a free running end with a surgical suture needle attached thereto:

a. inserting the surgical suture needle into the retaining means of the windowed end flap.

33. A method of manufacturing a device for holding a surgical device as in claim 32, wherein the retaining means is a small slit.

34. A method of manufacturing a device for holding a surgical device as in claim 32, wherein the retaining means is a foam pad adhesively affixed to the windowed end flap.

35. A method of manufacturing a device for holding a surgical device as in claim 30, further comprising the following steps, which occur after step h, i. sterilizing the surgical device; and j. packaging the device in at least one packaging system.

36. A method of manufacturing a device for holding a surgical device as in claim 35, wherein the package system comprises a hermetically sealed, peelable, outer package, the ends of which are not sealed to provide an opening means.

37. A method of manufacturing a device for holding a surgical device as in claim 36, wherein the outer package is made of a combination of medical grade paper and polyester/propylene sheeting.

38. A method of manufacturing a device for holding a surgical device as in claim 36, wherein the outer package is made of a combination of mylar and tyvek.

39. A method of manufacturing a device for holding a surgical device as in claim 36, wherein the packaging system further comprises a hermetically sealed, peelable, inner moisture impervious barrier, the ends of which are not sealed to provide an opening means.

40. A method of manufacturing a device for holding a surgical device as in claim 39, wherein the moisture impervious barrier is made of metal foil.

\* \* \* \* \*

UNITED STATES PATENT AND TRADEMARK OFFICE
CERTIFICATE OF CORRECTION

PATENT NO.    : 6,409,016 B1
DATED         : June 25, 2002
INVENTOR(S)   : Michael Braginsky et al.

It is certified that error appears in the above-identified patent and that said Letters Patent is hereby corrected as shown below:

Column 3,
Line 22, replace "a plurality of slits 17, 19 and ," with -- a plurality of slits 17, 19 and perforation 24 --;
Line 24, replace "at a proximal 6 1and a distal end 62" with -- at a proximal 61 and a distal end 62 with --;

Column 4,
Line 7, replace "tube. shaped device" with -- tubed-shaped device --;

Column 5,
Line 26, replace "tactile feel, es, ripples," with -- tactile feel, eg, ripples --;
Line 46, replace "comer of the end" with -- corner of the end --.

Signed and Sealed this

Seventh Day of January, 2003

JAMES E. ROGAN
*Director of the United States Patent and Trademark Office*